(12) United States Patent
Roger

(10) Patent No.: US 7,530,997 B2
(45) Date of Patent: May 12, 2009

(54) HEART VALVE

(75) Inventor: Gregory James Roger, St. Leonards (AU)

(73) Assignee: Advanced Surgical Design and Manufacture Limited, St. Leonards, New South Wales (AU)

( * ) Notice: Subject to any disclaimer, the term of this patent is extended or adjusted under 35 U.S.C. 154(b) by 0 days.

(21) Appl. No.: 10/586,883

(22) PCT Filed: Jan. 21, 2005

(86) PCT No.: PCT/AU2005/000067

§ 371 (c)(1),
(2), (4) Date: Apr. 13, 2007

(87) PCT Pub. No.: WO2005/070342

PCT Pub. Date: Aug. 4, 2005

(65) Prior Publication Data

US 2007/0276479 A1 Nov. 29, 2007

(30) Foreign Application Priority Data

Jan. 22, 2004 (AU) .............................. 2004900302

(51) Int. Cl.
*A61F 2/24* (2006.01)
(52) U.S. Cl. ............... 623/2.38; 623/2.39; 623/2.17
(58) Field of Classification Search ............... 623/2.17, 623/2.38, 2.39, 2.1, 2.2, 2.13; *A61F 2/24*
See application file for complete search history.

(56) References Cited

U.S. PATENT DOCUMENTS

| 3,835,475 | A | * | 9/1974 | Child | 623/2.23 |
| 3,839,741 | A | * | 10/1974 | Haller | 623/2.34 |
| 4,599,081 | A | | 7/1986 | Cohen | |
| 4,995,881 | A | * | 2/1991 | Knoch et al. | 623/2.29 |
| 5,002,567 | A | | 3/1991 | Bona et al. | |
| 5,197,980 | A | | 3/1993 | Gorshkov et al. | |
| 5,401,255 | A | * | 3/1995 | Sutherland et al. | 604/247 |
| 5,500,014 | A | * | 3/1996 | Quijano et al. | 623/1.24 |
| 5,861,029 | A | | 1/1999 | Evdokimov et al. | |
| 6,200,341 | B1 | * | 3/2001 | Jones et al. | 623/2.39 |
| 6,358,278 | B1 | * | 3/2002 | Brendzel et al. | 623/2.39 |
| 6,468,305 | B1 | * | 10/2002 | Otte | 623/2.4 |
| 7,147,663 | B1 | * | 12/2006 | Berg et al. | 623/2.38 |
| 7,217,287 | B2 | * | 5/2007 | Wilson et al. | 623/2.11 |
| 2004/0039442 | A1 | * | 2/2004 | St. Goar et al. | 623/2.36 |
| 2004/0092858 | A1 | * | 5/2004 | Wilson et al. | 604/9 |
| 2004/0127979 | A1 | * | 7/2004 | Wilson et al. | 623/2.1 |

FOREIGN PATENT DOCUMENTS

WO  WO 01/34068 A1  5/2001

\* cited by examiner

*Primary Examiner*—Brian E Pellegrino
*Assistant Examiner*—Jason-Dennis Stewart
(74) *Attorney, Agent, or Firm*—Knobbe Martens Olson & Bear LLP

(57) ABSTRACT

A valve assembly (10) has a support ring (20) and a valve body (30). The valve body (30) is supported by the ring (20) and comprises an annular body portion (31) that is rotatably engageable with the support ring (20). The annular body portion (30) supports a plurality of leaflets (32) that are moveable relative to each other and the annular body portion (30) between: a closed position and an open position upon changes in pressure differential across the valve assembly (10).

27 Claims, 5 Drawing Sheets

HEART VALVE

CROSS-REFERENCE TO RELATED APPLICATIONS

The present application claims priority from Provisional Patent Application No 2004900302 filed on 22 Jan. 2004, the content of which is incorporated herein by reference.

TECHNICAL FIELD

The present invention relates to the field of devices for replacing the function of a valve in the cardiovascular system, in particular the major valves of the heart.

BACKGROUND ART

Valves of the heart are currently replaced either by artificial valves of a range of designs or animal tissue valves, with or without some artificial material incorporated. Both artificial valves using artificial materials and biological materials have shortcomings including the need for lifelong anti-coagulation to prevent the formation of clots in the eddies formed by the mechanical function of the valves, potential for mechanical wear and/or failure, release of wear debris into the bloodstream, excessive noise and difficulties encountered during implantation. Further shortcomings include destruction of red blood cell cells as blood passes through such mechanical valves.

Tissue valves are difficult to manufacture and require harvesting suitable tissue, the need to treat the tissue to prevent the transmission of infective agents. Further, such valves suffer the degradation of tissue with time through either immune response or calcification as well as difficulties encountered during implantation.

The present invention aims to address the problems encountered with the prior art valves.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In a first aspect, the present invention is a valve assembly comprising:
a support ring having an outer surface and an inner surface;
a valve body comprising an annular body portion supporting a plurality of moveable leaflets that are moveable relative to the annular body portion and to each other between a first closed position and at least one second open position defining a first fluid pathway through the assembly when subject to a first pressure differential across the body;
wherein the annular body portion is mountable to the inner surface of the support ring and is relatively rotatable thereto.

The valve assembly of the present invention has a number of medical and industrial applications including a valve assembly for the cardiovascular system of a human or animal subject. It should be appreciated, however, that the valve assembly is not limited to such an exemplary application and could be used industrially or in any other system.

In a second aspect, the present invention is a valve assembly for implantation in the cardio-vascular system of a human or animal subject, the valve assembly comprising:
a support ring having an outer surface and an inner surface, the outer surface being engageable with the wall of a vessel of the human or animal subject; and
a valve body comprising an annular body portion supporting a plurality of moveable leaflets that are moveable relative to the annular body portion and to each other between a first closed position and at least one second open position defining a first fluid pathway through the assembly when subject to a first pressure differential across the valve body;
wherein the annular body portion is mountable to the inner surface of the support ring and is relatively rotatable thereto.

When the valve assembly is subjected to a second pressure differential, the plurality of leaflets may move to their first closed position.

The first pressure differential may comprise a region of higher pressure upstream of the valve assembly relative to a lower pressure downstream of the valve. The second pressure differential may comprise a region of lower pressure upstream of the valve assembly relative to a region of higher pressure downstream of the valve assembly.

When the valve assembly is implanted into the cardiovasculature of the heart of a subject, the first pressure differential may correspond to systole (the pumping phase of the heart) of a patient's heart, and the second pressure differential may correspond to diastole (the filling phase of the heart) or vice versa depending upon the positioning of the valve within the system.

In addition to being rotatable relative to the support ring, the annular body portion may also be moveable relative to the support ring from a sealed position to at least one unsealed position.

In the unsealed position, the annular body and the support ring may define a second fluid pathway through the assembly when the assembly is subjected to the first pressure differential. Typically, when in the unsealed position, the annular body portion is not in engagement with the support ring. Because there is no engagement between the annular body portion and the support ring, there is minimal resistance to the rotation of the annular body portion relative to the support ring. Essentially, the annular body portion is free to rotate relative to the support ring and the support ring and the annular body portion form a hydrodynamic bearing lubricatable by fluid flowing through the valve.

The relatively higher upstream pressure of the first pressure differential typically causes the leaflets to move to their open position. The resultant flow of fluid through the first fluid pathway may cause rotation of both the leaflets and the annular body portion relative to the support ring. To optimise the rotation of leaflets and annular body portion, the leaflets may be inclined at an angle to the direction of fluid flow through the first fluid pathway when at least in the second open position. The rotating leaflets provide less resistance to the flow of fluid and decrease turbulence of the fluid flowing through the first fluid pathway. A fluid engaging surface portion of the leaflets may be convex or concave in shape to optimise rotation of the leaflets and the annular body portion. Further, a tip or an edge of at least one of the leaflets may be angled relative to the remainder of the leaflet. Such a configuration may have the advantage of minimising disruption of the flow of fluid at and around the tips and/or edges of the leaflets.

The first pressure differential may therefore cause the leaflets to move from a first closed position to a second open position. In the second open position, the leaflets are typically angled relative to the flow of fluid through the first fluid pathway thus causing rotation of the annular body portion relative to the support ring. The relatively high upstream pressure of the first pressure differential may also create a sufficient force to move the annular body portion from its sealed position to its unsealed position relative to the support ring. The fluid flowing through the second fluid pathway defined by the annular body portion in its unsealed position relative to the support ring continues to keep the annular body portion in the unsealed position during the first pressure differential phase.

When positioned in the vasculature of a subject, the valve will be subject to various pressures and pressure changes. The pulsatile nature of the heart may result in a period of high pressure upstream of the valve relative to the pressure downstream of the valve. The relatively high upstream pressure causes the leaflets of the valve assembly to move into their open position and the annular body portion commences rotation. The blood pumped by the heart may, therefore, flow through the valve assembly with minimal resistance. As the heart reaches the end of the pumping phase, the upstream pressure progressively decreases as the flow of blood from the heart decreases and the pressure differential across the valve assembly gradually changes. The relatively decreasing upstream pressure exerts a decreasing force on the leaflets of the valve and they commence a return to their first closed position. At the end of the pumping phase of the heart and as the upstream blood flow momentarily ceases, the leaflets may be almost in the closed position. The downstream pressure at this stage is relatively higher than the upstream pressure causing the leaflets to move to their fully closed position.

The leaflets may, therefore, move progressively upon progressive change of pressure between the first and the second pressure differentials. Such progressive movement in correlation with the pressure changes in the cardiovascular system has the advantage that the valve does not "snap" shut suddenly as the blood flow ceases. Such a sudden snapping motion of valves has the disadvantage of increasing the wear of the valve.

The leaflets may have a surface coating or the surface may have been treated so as to reduce turbulence of fluid flowing past and/or over the leaflets. Preferably, at least a portion of the surface of at least some of the leaflets is provided with a relative roughness factor or surface texture which enhances reduction of turbulence of fluid at and adjacent the surface of the leaflets.

The moveable leaflets may be hingedly connected to the annular body portion of the valve body. Alternatively, each of the plurality of moveable leaflets may be fixedly connected to the annular body portion of the valve body. In the latter embodiment, it is envisaged that the leaflets may be made, at least in part, from a deformable material. The leaflets may be integrally formed with the annular body portion or alternatively the moveable leaflets may by formed separately from the annular body portion. The leaflets may further be biased so as to assume the second position in the absence of the first pressure differential.

Each moveable leaflet may be generally triangular in shape. A first edge of each moveable leaflet may engage the annular body portion of the valve body and extend to a central tip, distal the annular body.

Preferably, the leaflets extend relatively inwardly of the annular body portion in the first closed position to form a substantially convex body. Each leaflet may overlap an adjacent leaflet such that there is no gap between the leaflets when the valve is in the closed position. In use, the convex body may be positioned extending away from the annular body portion and in a downstream direction. The convex body formed by the leaflets has the advantage of providing a relatively strong structure against any downstream pressure, for example, during the second pressure differential. When used in the vascular system of a subject, when the pumping phase of the heart ceases and the flow of blood upstream of the valve momentarily ceases, the pressure downstream of the valve is relatively higher than the upstream pressure causing a back pressure on the leaflets of the valve assembly. The convex shaped body formed by the leaflets in their closed position is structurally stronger than a relatively flat body of leaflets and thus the likelihood of leakage of blood back upstream is reduced.

The leaflets may be made from a biological material selected from the group comprising autologous graft tissue, allograft tissue and xenograft tissue.

Alternatively, the moveable leaflets may be made from an artificial material selected from the group comprising polymers, composites, metals and metal alloys. More preferably, the moveable leaflets are formed from Nitinol™.

The support ring may be formed from a ceramic, a metal or a metal alloy material. More preferably, the support ring is formed from a Cobalt-Chromium alloy.

The annular body portion of the valve body may be formed from a ceramic, a metal or a metal alloy material. More preferably the annular body portion is formed from a Cobalt-Chromium alloy.

The second fluid pathway is typically defined by the inner surface of the support ring and the annular body portion of the valve body as described above. Alternatively, the second fluid pathway may be defined by apertures in the annular body portion which are sealingly engaged with the inner surface of the support ring until application of the first pressure differential.

As described above, the first pressure differential causes the annular body portion of the valve body to move from a sealing engagement with the support ring to a position of non engagement between the annular body portion and the support ring. The second pressure differential causes the annular body portion of the valve body to move back into sealing engagement with the support ring.

Preferably, the annular body portion of the valve body moves between sealing engagement and non-engagement with the support ring progressively upon a progressive change between the first pressure differential and the second pressure differential.

The annular body portion may also include a plurality of furrows located at an outer peripheral edge of the annular body portion. During the first pressure differential, the furrows at the peripheral edge optimise rotation of the annular body portion relative to the support ring. Essentially, the furrows act as a turbine to optimise rotation of the body portion.

The support ring and/or the annular portion of the valve body may be coated with at least one of the group comprising an antibacterial, an anti-coagulant and a substance to prevent the overgrowth of tissue or combinations thereof.

The annular body portion and the support ring may be provided as a single unit for implant into a system or subject. Alternatively, the annular body portion may be provided as a separate component to the support ring. This embodiment has the advantage that the support ring may be implanted within a system as a first step. The annular body portion may then be subsequently mounted to the support ring. When the valve assembly is used to replace a valve in the cardiovascular system of a subject, this two part implantation has the advantage that the support ring may be secured in place and the tissue around the support ring allowed to heal prior to implanting the annular body portion.

The valve assembly of the present invention may be used to replace any valve of the cardiovascular system including the aortic valve, the pulmonary valve, the tricuspid valve and the mitral valve. Other peripheral vascular valves may be replaced by the valve assembly of the present invention.

In a third aspect, the present invention is a valve assembly for implantation in the cardio-vascular system of a human or animal subject, the assembly comprising:

a valve body comprising an annular body portion supporting a plurality of multi-sided leaflets that extend inwardly and away from the body portion;

wherein said leaflets are moveable relative to the annular body portion and each other between a first closed position and at least one second open position defining a first fluid pathway through the assembly when subject to a first pressure differential across the body.

According to a fourth aspect, the present invention is a valve for implantation in the cardio-vascular system of a human or animal subject, the assembly comprising:

a support ring having an outer surface and an inner surface, the outer surface engageable with the wall of a vessel of the human or animal subject; and a valve body comprising an annular body portion supporting a plurality of leaflets that are moveable relative to the annular body portion and to each other, the leaflets being moveable between a first closed position and at least one second opened position defining a first fluid flow pathway through the assembly when subject to a first pressure differential across the body;

wherein the annular body portion is mountable to the inner surface of the support ring and is relatively moveable from a sealed position to at least one unsealed position defining a second fluid pathway through the assembly when the assembly is subject to the first pressure differential.

In one embodiment of the fourth aspect, the annular body portion is also relatively rotatable with respect to the support ring.

In a fifth aspect, the present invention is a method of implanting a valve assembly within the cardio-vascular system of a patient; the method comprising delivering the valve assembly as defined herein to a surgical site within a vascular vessel of the patient.

The support ring may be delivered separately to the valve body. Preferably, the valve body is delivered to the surgical site and engaged with the support ring once the support ring is securely seated within the vascular vessel of the patient.

The support ring may be delivered to the surgical site through a catheter and/or the valve body is delivered to the surgical site through a catheter.

BRIEF DESCRIPTION OF THE DRAWINGS

By way of example only, preferred embodiments of the invention are now described with reference to the accompanying drawings, in which.

DESCRIPTION OF AN EXEMPLARY EMBODIMENT OF THE INVENTION

Figure 1:
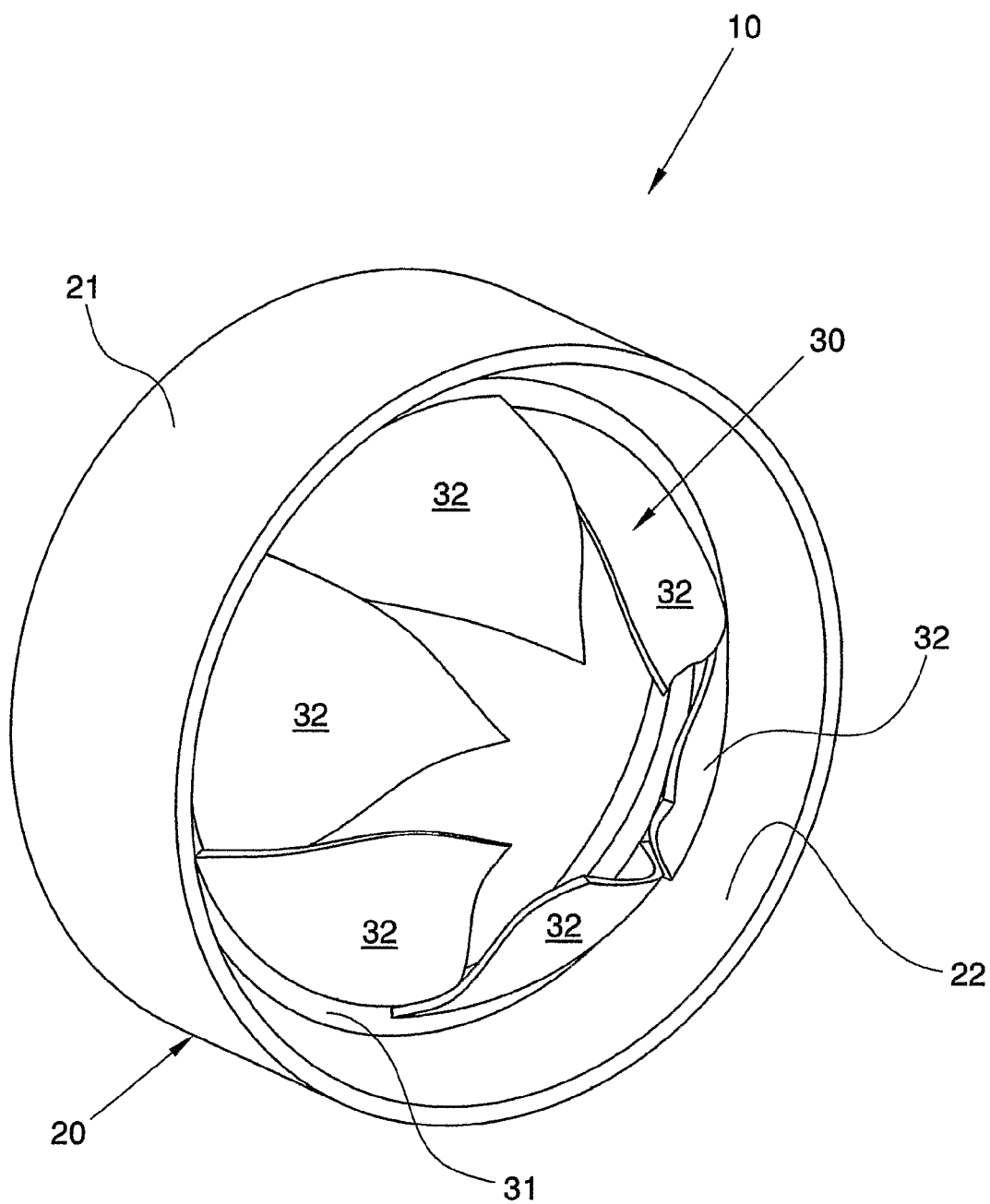
FIG. 1 is a perspective view of one embodiment of the valve assembly of the present invention.

The exemplary embodiment depicted is a valve assembly for replacing a vascular valve of a subject. As shown in FIG. 1, valve assembly 10 for the vascular system of a subject according to the present invention includes a support ring 20 having an outer surface 21 for engagement with a wall of a vascular vessel of a patient and an inner surface 22. A valve body 30 is supported by the ring 20 and comprises an annular body portion 31 that is rotatably engageable with the inner surface 22 of the support ring 20. The valve body 30 also comprises a plurality of moveable leaflets 32.

Figure 2A:
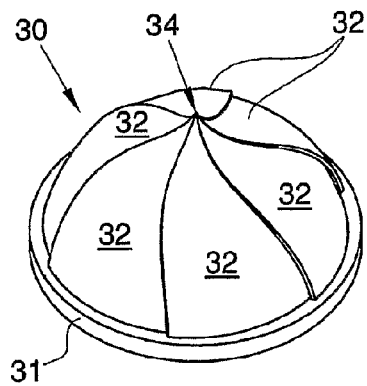
FIGS. 2(a)-(f) are perspective, side and plan views of the valve body of the present invention.
Figure 2B:
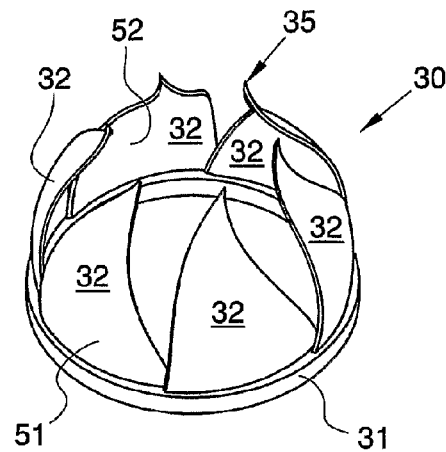
Figure 2C:
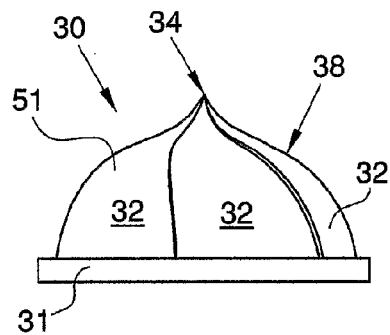
Figure 2D:
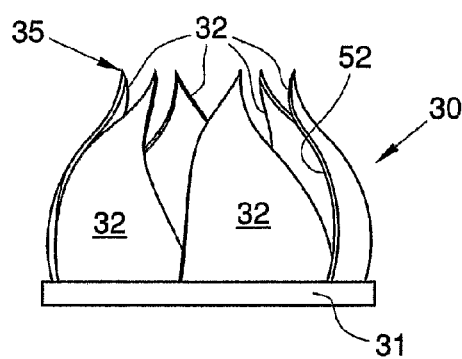
Figure 2E:
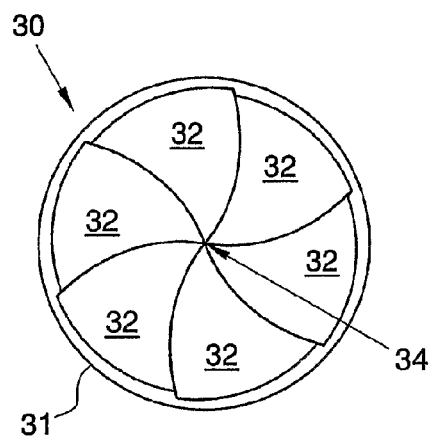
Figure 2F:
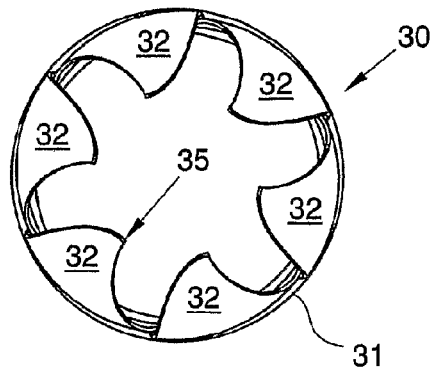

FIGS. 2a to 2f depict examples of the valve body 30 of the present invention. FIG. 2(a) depicts the leaflets 32 in the first or closed position 34 while FIG. 2(b) shows the moveable leaflets in a second or open position 35. A side view of the valve body 30 is shown in FIGS. 2(c) and 2(d) wherein the moveable leaflets 32 are again shown in the first or closed position 34 and in the second or closed position 35. FIGS. 2(e) and 2(f) provide a plan view of the valve body 30 with again the moveable leaflets 32 being in the first or closed position 34 and in the second or open position 35.

Figure 3A:
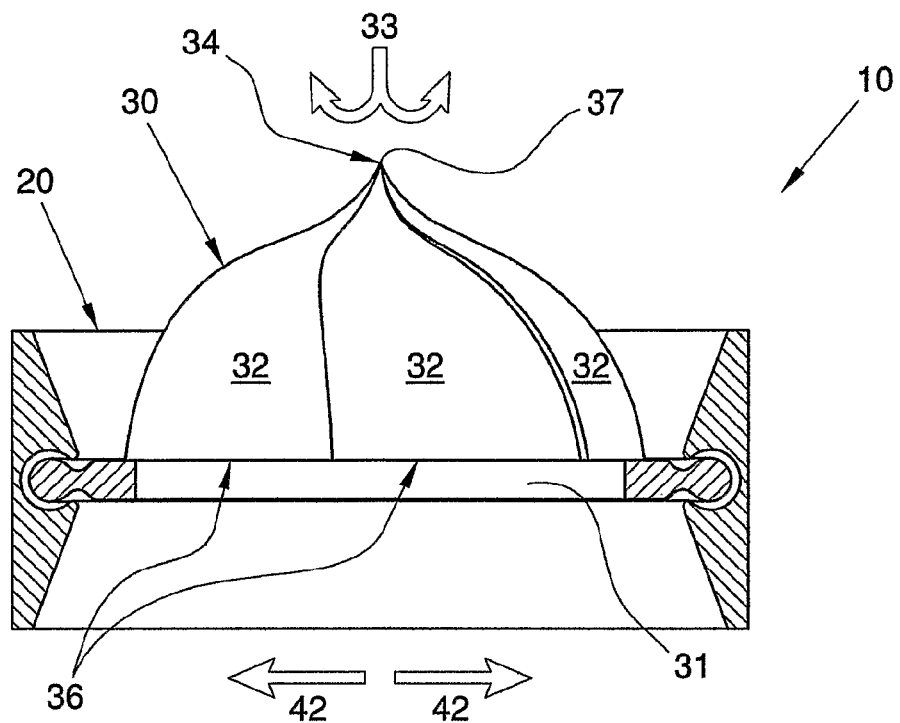
FIGS. 3(a) and 3(b) are side views of the valve assembly of FIG. 1.
Figure 3B:
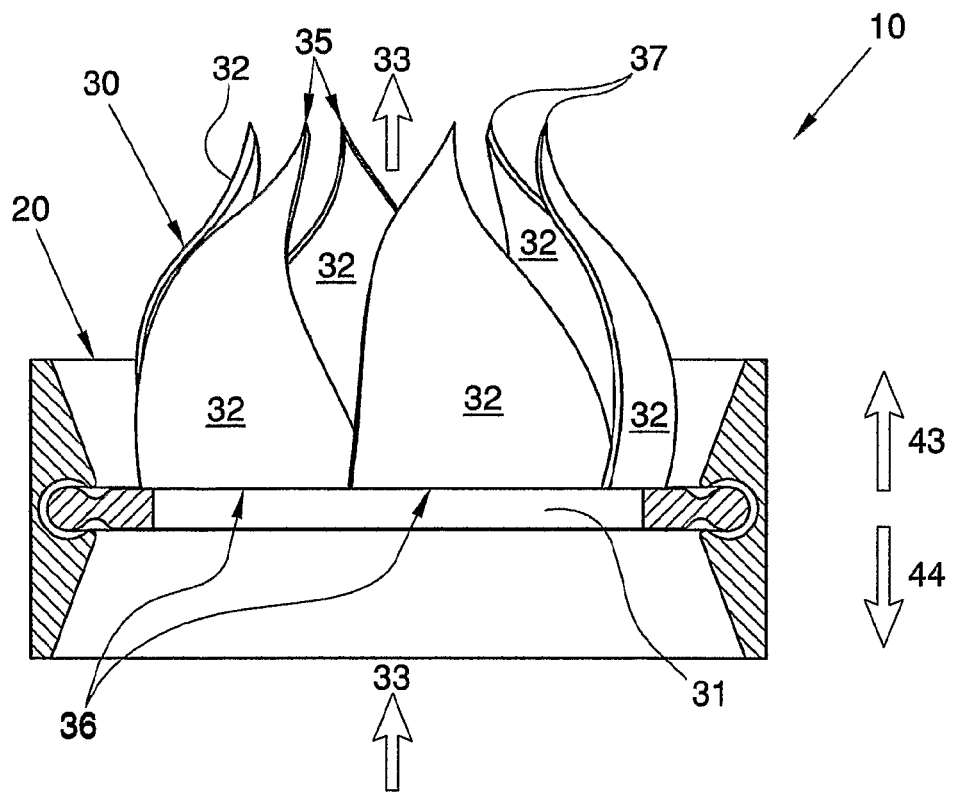

An example of the operation of the valve body 30 is depicted in FIGS. 3(a) and 3(b). When in the second or open position 35, as shown in FIG. 3(b), the moveable leaflets 32 provide a first fluid pathway represented by arrow 33 through the valve assembly 10. When the leaflets 32 are in the first or closed position 34, the moveable leaflets 32 work together to occlude the first fluid pathway 33 as shown in FIG. 3(a), occluding blood flow through the valve in the opposite direction as shown by the arrow denoting the direction of flow through the first fluid pathway 33.

In this example, the moveable leaflets 32 are arranged such that upon subject to the first pressure differential across the valve body, blood flow through the first fluid pathway 33 causes the leaflets and the annular body portion 31 to rotate with respect to the support ring 20. The leaflets 32 are angled relative to the direction of blood flow through the first fluid pathway 33 and are caused to rotate which in turn rotates the annular body portion 31 with respect to the support ring 20 as blood flows past the leaflets 32 through the first fluid pathway 33. As depicted in FIGS. 2(a) and 2(b), the leaflets are substantially cup-shaped with an outer convex surface 51 and an inner concave surface 52.

The plurality of moveable leaflets 32 are configured such that they move toward the second or open position 35 progressively upon progressive change of pressure from the first pressure differential to the second pressure differential. As the blood flow reduces at the end of systole the momentum of the rotating valve would then tend to start closing down as it drove against the relatively slower moving blood. As the blood flow ceases, momentarily before the pressure is exerted backwards on the valve, the moveable leaflets 32 are relatively close to the first or closed position 34 to occlude the first fluid pathway 33. This compares to all other valves where this is the moment at which shutting commences, so that the fall back pressure and leak is therefore higher and noisier as the valve snaps shut. This "snapping shut" is the cause of normal heart sounds in well functioning valves.

The plurality of moveable leaflets 32 may be hingedly engaged with the annular body portion 31 of the valve body 30 such that the plurality of moveable leaflets 32 are moveable from the first or closed position 34 toward the second or opened position 35 upon application of the first pressure differential across the valve assembly 10, and to the first or closed position 34 upon application of the second pressure differential.

Alternatively, the plurality of moveable leaflets 32 may be affixedly engaged with the annular body portion 31 of the valve body 30 and be formed from a deformable material such that the plurality of moveable leaflets 32 move from the first position 34 toward the second position 35 upon application of the first pressure, and to the first position 34 upon application of the second pressure differential.

The plurality of moveable leaflets 32 may be formed from a biological material selected from the group comprising autologous graft tissue, allograft tissue and xenograft tissue, or alternatively, the plurality of moveable leaflets 32 may be formed from an artificial material selected from the group comprising polymers, composites, metals and metal alloys, for example Nitinol™. The moveable leaflets 32 may be textured and/or coated to limit turbulence and blood clotting tendencies.

The plurality of moveable leaflets 32 may be provided with a surface coating or a surface treatment so as to at least reduce turbulence of blood flowing past and/or over the leaflets. Such a surface treatment or coating may provide reduction in turbulence within blood passing through the first fluid pathway 33. At least a portion of the surface of at least some of the leaflets 32 may be provided with a relative roughness factor or surface texture which enhances reduction of turbulence of blood at and adjacent the surface of the leaflets 32. Reduction of turbulence and of blood through the first fluid pathway 33 may reduce the amount of and/or necessity of the use anticoagulant compounds.

In this example, each moveable leaflet 32 is generally triangular in shape with a first edge 36 of each moveable leaflet being engaged with the annular body portion 31 of the valve body 30, and a central tip 37 of each moveable leaflet being positioned distal the annular body portion 31 of the valve body 30 in the first direction 43. The plurality of moveable leaflets 32 form a convex structure 38 extending from the annular body portion 31 of the valve body 30 in the first direction 43 when in the first position 34.

Each moveable leaflet 32 moves radially outwardly 42 toward the second position 35 upon application of the first pressure differential so as to reduce the occurrence of turbulence within the blood of the vascular vessel 40. The central tips of the moveable leaflets may be shaped so as to further reduce the occurrence of turbulence within the blood.

The support ring 20 may be formed from a ceramic, a metal or a metal alloy material for example a Cobalt-Chromium alloy. The annular body portion 31 of the valve body 30 may be formed from a ceramic, a metal or a metal alloy material for example a Cobalt-Chromium alloy. The support ring 20 and/or the annular body portion 31 of the valve body 30 may include a coating for example an antibacterial, anti-coagulant or anti-tissue on-growth coating or a combination of coatings.

A further example of the cardio-vascular valve 10 and valve body 30 of FIGS. 1-3 is depicted in FIGS. 4(a)-(d). In this arrangement, a second fluid pathway 39 is provided between the inner annular portion 22 of the support ring 20 and the annular body portion 31 of the valve body 30.

Figure 4A:
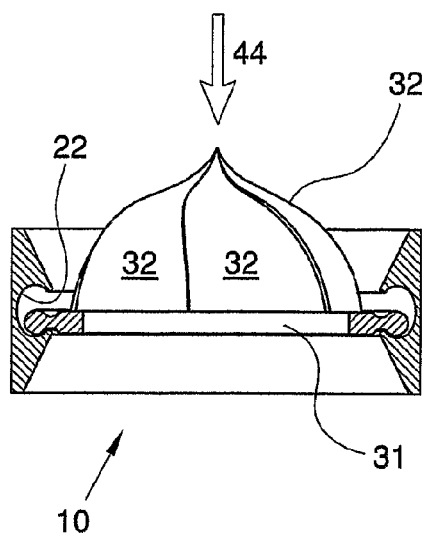
FIGS. 4(a)-(d) are side views of a further example of the valve assembly in accordance with the present invention.
Figure 4B:
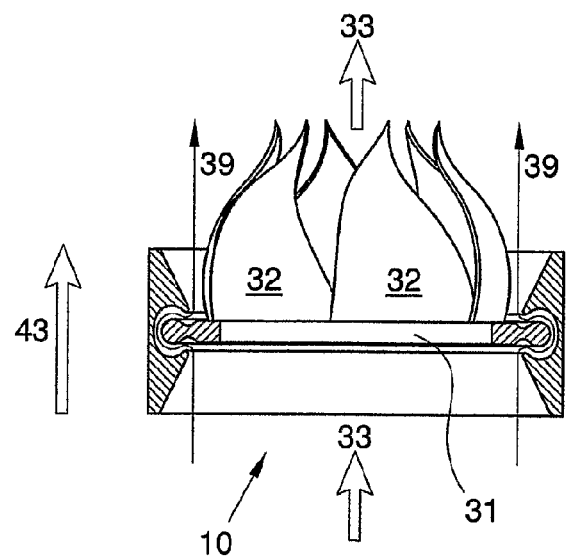

During the first pressure differential, the annular body portion 31 of the valve body 30 moves in the first direction 33 from a position wherein the annular body portion engages the inner annular portion 22 of the support ring 20 to a position of non-engagement between the two components of the assembly. This displacement of the annular body portion provides the second fluid pathway 39 as shown in FIG. 4(b). The force of the fluid flow during a first pressure differential keeps the annular body portion in a non-engaging position as shown in FIG. 4b i.e. the annular body portion is free floating relative to the support ring. This embodiment of the invention further optimises rotation of the annular body portion relative to the support ring 20, that is, friction between the two components is avoided. During the second pressure differential, the annular body portion 31 of the valve body 30 moves in a second direction 44 and back into engagement with the support ring 20. This engagement between the two components occludes blood flow through the second fluid pathway 39 in the second direction 44 as shown in FIG. 4(a). The annular body portion 31 of the valve body 30 moves in the second direction 44 progressively upon progressive change of pressure from the first pressure differential to the second pressure differential.

Figure 4C:
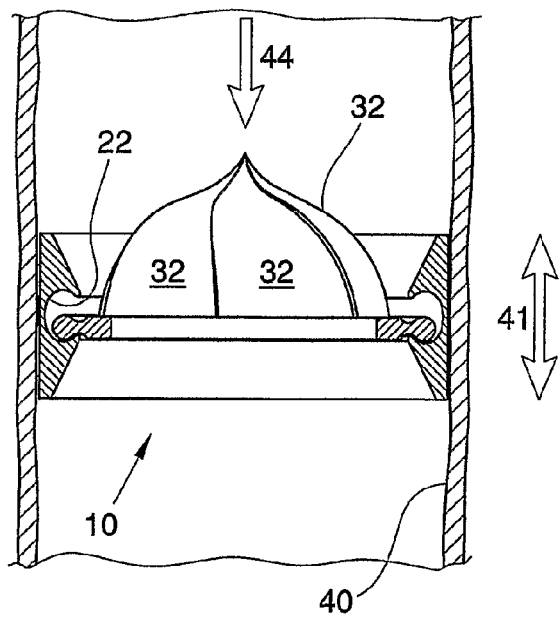
Figure 4D:
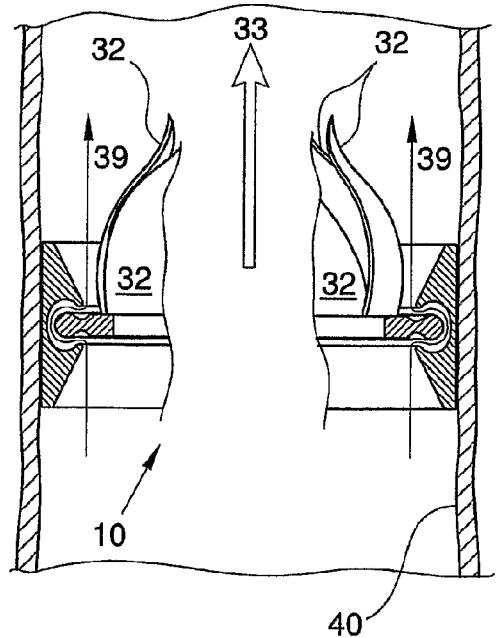

An example of the cardio-vascular valve of FIGS. 4(a) and 4(b) when engaged with the wall of a vascular vessel 40 of a patient is shown in FIGS. 4(c) and 4(d). In this example, each of the plurality of moveable leaflets 32 are inclined to the longitudinal axis 41 of the vascular vessel 40 and extend from the annular body portion 31 of the valve body 30 in a first direction 43, and each moveable leaflet 32 overlaps at least on adjacent leaflet when moved to the second position 35 so as to occlude blood flow.

Figure 5A:
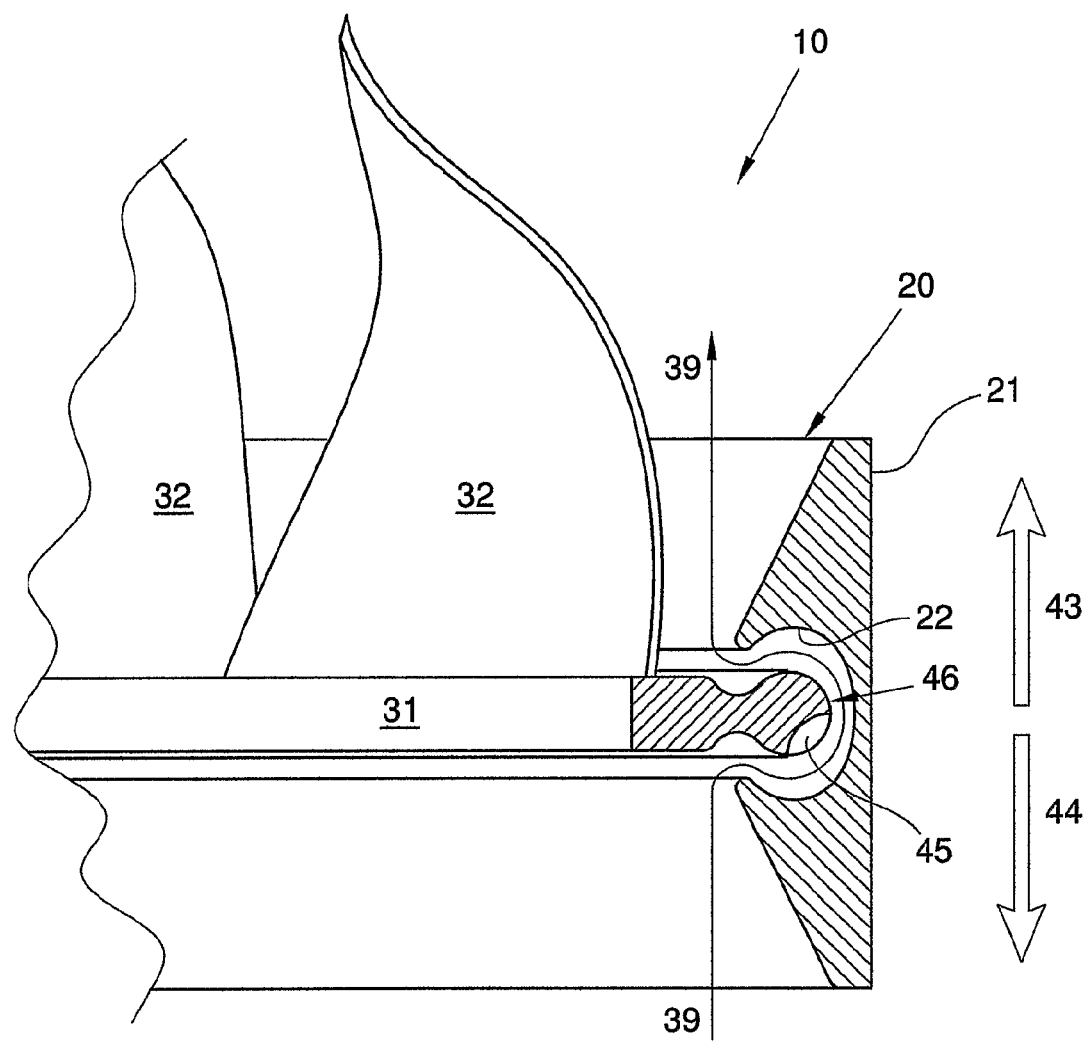
FIGS. 5(a) and (b) are enlarged part-sectional views of the valve assembly of FIG. 4.
Figure 5B:
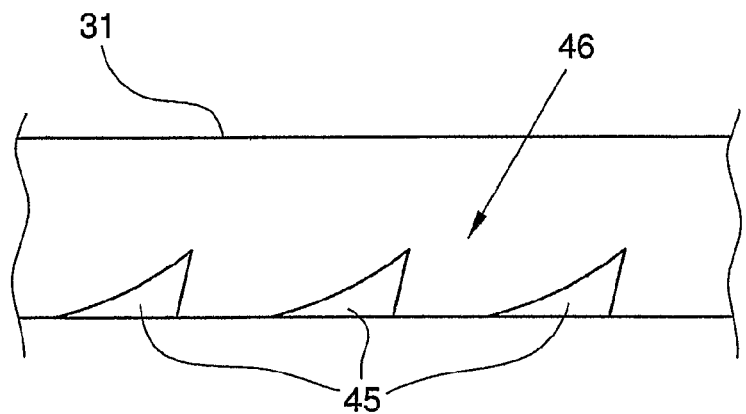

FIG. 5(a) is an enlarged part-sectional view of the valve assembly 10 of FIG. 3. In this example, the annular body portion 31 includes a plurality of furrows 45 located at an outer peripheral edge 46 of the annular body portion 31 such that blood flow through the second fluid pathway 39 further causes the valve body 30 to rotate relative to the support ring 20 upon application of the first pressure differential, that is, the furrows act as a turbine to enhance rotation during the first pressure differential. FIG. 5(b) shows a portion of the annular body portion 31 having a plurality of furrows 45 located at the outer peripheral edge 46 of the annular body portion 31.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A valve assembly comprising:
a support ring having an outer surface and an inner surface;
a valve body comprising an annular body portion supporting a plurality of moveable leaflets that are moveable relative to the annular body portion and to each other between a first closed position and at least one second open position defining a first fluid pathway for the flow of fluid in a first direction across the assembly when subject to a first pressure differential across the body;
wherein the annular body portion is mountable to the inner surface of the support ring and is relatively rotatable thereto;
and further wherein the annular body portion is axially moveable relative to the support ring from a sealed position to at least one unsealed position, the annular body portion and the support ring, in the unsealed position together defining a second fluid pathway for the flow of fluid in said first direction across the assembly and wherein the annular body portion moves to its at least one unsealed position when the assembly is subjected to the first pressure differential.

2. The valve assembly of claim 1 wherein when the valve assembly is subjected to a second pressure differential, the plurality of leaflets move to their first closed position.

3. The valve assembly of claim 1 wherein the first pressure differential comprises a region of higher pressure upstream of the valve assembly relative to a lower pressure downstream of the valve.

4. The valve assembly of claim 1 wherein the second pressure differential comprises a region of lower pressure upstream of the valve assembly relative to a region of higher pressure downstream of the valve assembly.

5. The valve assembly of claim 1 wherein the annular body portion is not in engagement with the support ring in its unsealed position.

6. The valve assembly of claim 1 wherein the leaflets extend inwardly from and at an angle to the annular body portion when in their closed position.

7. The valve assembly of claim 6 wherein the leaflets together form a convex body that extends in a first direction away from the annular body portion when the leaflets are in their closed position.

8. The valve assembly of claim 1 wherein at least one leaflet overlaps at least a portion of adjacent leaflet when in their first closed position.

9. The valve assembly of claim 1 wherein the leaflets move progressively upon progressive change of pressure between the first pressure differential and the second pressure differential.

10. The valve assembly of claim 1 wherein at least one of the leaflets has a surface coating or the surface has been treated to reduce turbulence of fluid flowing past and/or over the leaflets.

11. The valve assembly of claim 1 wherein the moveable leaflets are hingedly connected to the annular body portion of the valve body.

12. The valve assembly of claim 1 wherein the moveable leaflets are fixedly connected to the annular body portion of the valve body.

13. The valve assembly of claim 1 wherein the leaflets are made from a biological material selected from the group comprising autologous graft tissue, allograft tissue and xenograft tissue.

14. The valve assembly of claim 1 wherein the moveable leaflets are made from an artificial material selected from the group comprising polymers, composites, metals and metal alloys including Nitinol™.

15. The valve assembly of claim 1 wherein the support ring is made from a ceramic, a metal or a metal alloy material including a Cobalt-Chromium alloy.

16. The valve assembly of claim 1 wherein the annular body portion is made from a ceramic, a metal or a metal alloy material including a Cobalt-Chromium alloy.

17. The valve assembly of claim 1 wherein the annular body portion includes a turbine member to optimize rotation of the annular body portion.

18. The valve assembly of claim 1 wherein the annular body portion and the support ring are provided as a single unit for implant into a system or subject.

19. The valve assembly of claim 1 wherein the annular body portion and the support ring are provided as separate components.

20. The valve assembly of claim 1 installed as any valve of the cardiovascular system including the aortic valve, the pulmonary valve, the tricuspid valve and the mitral valve.

21. A method of implanting a valve assembly within the cardiovascular system of a patient; the method comprising delivering the valve assembly of claim 1 within a vascular vessel of the patient.

22. The method of claim 21 wherein the support ring is delivered separately to the valve body and as a first step.

23. A valve assembly for implantation in the cardio-vascular system of a human or animal subject, the valve assembly comprising:
   a support ring having an outer surface and an inner surface, the outer surface being engageable with the wall of a vessel of the human or animal subject; and
   a valve body comprising an annular body portion supporting a plurality of moveable leaflets that are moveable relative to the annular body portion and to each other between a first closed position and at least one second position defining a first fluid pathway for the flow of fluid in a first direction across the assembly when subject to a first pressure differential across the valve body;
   wherein the annular body portion is mountable to the inner surface of the support ring and is relatively rotatable thereto;
   and further wherein the annular body portion is axially moveable relative to the support ring from a sealed position to at least one unsealed position, the annular body portion and the support ring, in the unsealed position, together defining a second fluid pathway for the flow of fluid in said second direction across the assembly and wherein the annular body portion moves to its at least one unsealed position when the assembly is subjected to the first pressure differential.

24. A method of implanting a valve assembly within the cardiovascular system of a patient; the method comprising delivering the valve assembly of claim 23 within a vascular vessel of the patient.

25. A valve for implantation in the cardiovascular system of a human or animal subject, the assembly comprising:
   a support ring having an outer surface and an inner surface, the outer surface being engageable with the wall of a vessel of the human or animal subject; and
   a valve body comprising an annular body portion supporting a plurality of leaflets that are moveable relative to the annular body portion and to each other, the leaflets being moveable between a first closed position and at least one second opened position defining a first fluid flow pathway through the assembly when subject to a first pressure differential across the body;
   wherein the annular body portion is mountable to the inner surface of the support ring and is axially moveable from a sealed position to at least one unsealed position defining a second fluid pathway through the assembly when the assembly is subject to the first pressure differential.

26. The valve of claim 25 wherein the annular body portion is also relatively rotatable with respect to the support ring.

27. A method of implanting a valve assembly within the cardiovascular system of a patient; the method comprising delivering the valve assembly of claim 25 within a vascular vessel of the patient.

* * * * *

UNITED STATES PATENT AND TRADEMARK OFFICE
CERTIFICATE OF CORRECTION

PATENT NO. : 7,530,997 B2
APPLICATION NO. : 10/586883
DATED : May 12, 2009
INVENTOR(S) : Gregory James Roger It is certified that error appears in the above-identified patent and that said Letters Patent is hereby corrected as shown below:

At Column 9, Line 8, please delete "1" and insert therefore, --2--.

At Column 9, Line 21, please delete "closed" and insert therefore, --first closed--.

At Column 9, Line 23, please delete "adjacent" and insert therefore, --an adjacent--.

Signed and Sealed this

Twenty-second Day of December, 2009

David J. Kappos
*Director of the United States Patent and Trademark Office*